United States Patent
Randall et al.

(10) Patent No.: US 8,546,314 B2
(45) Date of Patent: Oct. 1, 2013

(54) SURFACE TREATMENT COMPOSITIONS INCLUDING POLYQUATERNIUM-22 AND SHEILDING SALTS

(71) Applicant: The Procter & Gamble Company, Cincinnati, OH (US)

(72) Inventors: Sherri Lynn Randall, Hamilton, OH (US); Michelle Ann Tscheiner, Cheviot, OH (US); Eric Scott Johnson, Hamilton, OH (US); Mark Robert Sivik, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 13/669,520

(22) Filed: Nov. 6, 2012

(65) Prior Publication Data

US 2013/0123161 A1    May 16, 2013

Related U.S. Application Data

(60) Provisional application No. 61/558,480, filed on Nov. 11, 2011.

(51) Int. Cl.
*C11D 3/37* (2006.01)
*C11D 1/83* (2006.01)

(52) U.S. Cl.
USPC ........... 510/127; 510/119; 510/276; 510/289; 510/290; 510/308; 510/340; 510/356; 510/421; 510/422; 510/426; 510/427

(58) Field of Classification Search
USPC ............. 510/119, 127, 276, 289, 290, 308, 510/340, 356, 421, 422, 426, 427
See application file for complete search history.

(56) References Cited

U.S. PATENT DOCUMENTS

| 6,753,307 B1* | 6/2004 | Panandiker et al. ........ 510/475 |
| 2010/0120655 A1 | 5/2010 | Kischkel et al. |
| 2011/0028373 A1* | 2/2011 | Fossum et al. ............. 510/236 |
| 2011/0319314 A1* | 12/2011 | Labeque et al. ............. 510/527 |

OTHER PUBLICATIONS

U.S. Appl. No. 13/669,526, filed Nov. 6, 2012 Randall, et al.

* cited by examiner

*Primary Examiner* — Charles Boyer
(74) *Attorney, Agent, or Firm* — Melissa G. Krasovec; Steven W. Miller

(57) ABSTRACT

A surface treatment composition comprising from about 6% to about 20%, by weight of the composition, of cationic polymer; from about 6% to about 40%, by weight of the composition, of anionic surfactant; and from about 4% to about 15%, by weight of the composition, of a shielding salt, wherein the weight ratio of anionic surfactant to cationic polymer is between about 0.5:1 and about 4:1. The shielding salt is defined by having a molecular weight of from about 25 to about 500 and being incapable of lowering the surface tension of water below 50 mN/m when added to water at concentrations of up to 0.01M.

11 Claims, No Drawings

SURFACE TREATMENT COMPOSITIONS INCLUDING POLYQUATERNIUM-22 AND SHEILDING SALTS

TECHNICAL FIELD

The present invention relates to surface treatment compositions containing a shielding salt. Specifically the invention relates to surface treatment compositions comprising a cationic polymer, an anionic surfactant, a shielding salt, and other selected ingredients where the shielding salt prevents the phase separation typically seen in cationic-anionic systems.

BACKGROUND

Conventional treatment compositions include cationic polymers and anionic surfactants because the combinations of these components can yield benefits to the surfaces, for example, fabrics, being cleaned. Specifically, this benefit may be achieved by complexing the cationic polymer with the anionic surfactant to form a precipitate complex is known as a "coacervate."

Coacervates can deliver various benefits familiar to one of ordinary skill in the art, for example, fabric softening. Additionally, coacervates are especially effective at rejuvenating fabric. Many clothing items are known to lose their color and fade over time, which frustrates consumers, because the clothing no longer matches the appearance as when originally acquired.

During the wash cycle, coacervates are deposited on the fabric surface and re-set the fibers or fibrils. Re-setting the fibers or fibrils is believed to result in smoother yarn, reducing the number of fibers protruding from the fabric surface. Protruding fibers or fibrils are able to scatter light, and produce an optical effect of diminished color intensity. Thus, re-setting these fibers results in less light scattering and a more intense perceived color.

The problem which arises is that formation of coacervate within the product bottle or container yields an undesirable product which is undesirably thick and difficult to pour or dispense. Further, settling of a coacervate in the product could lead to a variable benefit profile across doses as the consumer uses the product. Conventional formulations have minimized the amount of cationic polymer to 5% by weight or less of cationic polymer to minimize this undesirable overproduction of coacervate. However, by minimizing the amount of cationic polymer, the conventional formulations also lose some of the surface treatment benefits achieved when greater amounts of cationic polymer are included. Thus, there is a need for a surface treatment composition that includes higher levels of both cationic polymer and anionic surfactant to achieve improved surface treatment benefits without yielding undesirable coacervates in the packaged composition.

SUMMARY

Without being bound by theory, it has been surprisingly found that inclusion of a shielding salt with higher levels of both cationic polymer and anionic surfactant substantially precludes the formation of coacervates within the bottle, but allows for coacervate formation upon dilution.

In accordance with one embodiment of the present invention, a surface treatment composition is provided. The surface treatment composition comprises from about 6% to about 20%, by weight of the composition, of cationic polymer, from about 6% to about 40%, by weight of the composition, of anionic surfactant, and from about 4% to about 15%, by weight of the composition, of a shielding salt, wherein the shielding salt has a molecular weight of from about 25 to about 500, and is incapable of lowering the surface tension of water below 50 mN/m when added to water at concentrations of up to 0.01M. The surface treatment composition also has a weight ratio of anionic surfactant to cationic polymer of between about 0.5:1 and about 4:1.

These and additional objects and advantages provided by the embodiments of the present invention will be more fully understood in view of the following detailed description.

DETAILED DESCRIPTION

Definitions

As used herein, the term "coacervate" includes both liquid and solid phase separation.

As used herein, "surface" may include such surfaces such as fabric, dishes, glasses, and other cooking surfaces, hard surfaces, hair or skin. As used herein, the terms "fabric", "textile", and "cloth" are used non-specifically and may refer to any type of flexible material consisting of a network of natural or artificial fibers, including natural, artificial, and synthetic fibers, such as, but not limited to, cotton, linen, wool, polyester, nylon, silk, acrylic, and the like, including blends of various fabrics or fibers. As used herein "hard surface" includes hard surfaces being found in a typical home such as hard wood, tile, ceramic, plastic, leather, metal, glass. Such methods of use include the steps of contacting the composition, in neat form or diluted in wash liquor, with at least a portion of a surface then optionally rinsing the targeted surface. Optionally the targeted surface is subjected to a washing step prior to the aforementioned optional rinsing step. For purposes of the present invention, washing includes, but is not limited to, scrubbing, wiping and mechanical agitation.

As used herein, the phrase "surface treatment compositions" includes, but is not limited to, compositions delivered in laundry cleaning compositions and detergents, fabric softening compositions, fabric enhancing compositions, fabric freshening compositions, laundry prewash compositions, laundry pretreat compositions, or other laundry additives. Such compositions may be used as a pre-laundering treatment, a post-laundering treatment, or may be added during the rinse or wash cycle of the laundering operation. Moreover, the surface treatment compositions may be stored in single dose units, multi-dose bottles or containers.

As used herein and described below, "shielding salts" refer to salts that sequester or maintain separation between anionic surfactants and cationic polymers inside the product container or bottle in order to reduce coacervate formation inside the bottle.

As used herein, the molecular weight, sometimes abbreviated as MW, of a polymer refers to the polymer's weight average molecular weight, unless otherwise noted.

Embodiments of the present invention generally relate to surface treatment compositions comprising cationic polymer, anionic surfactant, and one or more shielding salts. The surface treatment compositions comprise at least about 6% by weight of cationic polymer, at least about 6% by weight anionic surfactant, and at least about 4% by weight of the shielding salt. The weight ratio of anionic surfactant to cationic polymer is between about 0.5:1 and about 4:1. The composition may also have a weight ratio of shielding salt to cationic polymer of between about 0.3:1 and about 3:1. In certain embodiments, the surface treatment composition is a fabric treatment composition.

Without being bound by theory, the shielding salt is able to mitigate the electrostatic attraction between the cationic polymer and the anionic surfactant. Formulating compositions with levels of a shielding salt at about 4 weight percent or greater allows the shielding salt to electrostatically screen the polymer from the surfactant. If the salt contains a hydrophobic moiety, it may also reduce the hydrophobic interaction between the cationic polymer and the anionic surfactant. In exemplary embodiments described below, the shielding salt may be a hydrotrope which minimizes electrostatic and hydrophobic interactions between the cationic polymer and anionic surfactants. By the term "hydrotrope", it is meant that the salt has both hydrophilic and hydrophobic portions and as such can have hydrophobic interactions with surfactants and/or the hydrophobic portions of the polymer.

Anionic Surfactant

Suitable anionic surfactants may be any of the conventional anionic surfactant types typically used in liquid detergent products. Such surfactants include the alkyl benzene sulfonic acids and their salts as well as alkoxylated or non-alkoxylated alkyl sulfate materials. Exemplary anionic surfactants are the alkali metal salts of $C_{10}$-$C_{16}$ alkyl benzene sulfonic acids, preferably $C_{11}$-$C_{14}$ alkyl benzene sulfonic acids. In one aspect, the alkyl group is linear. Such linear alkyl benzene sulfonates are known as "LAS". Such surfactants and their preparation are described for example in U.S. Pat. Nos. 2,220,099 and 2,477,383. Especially preferred are the sodium and potassium linear straight chain alkylbenzene sulfonates in which the average number of carbon atoms in the alkyl group is from about 11 to 14. Sodium $C_{11}$-$C_{14}$ LAS, e.g., $C_{12}$ LAS, are a specific example of such surfactants.

Another exemplary type of anionic surfactant comprises linear or branched ethoxylated alkyl sulfate surfactants. Such materials, also known as alkyl ether sulfates or alkyl polyethoxylate sulfates, are those which correspond to the formula: $R'$—O—$(C_2H_4O)_n$—$SO_3M$ wherein $R'$ is a $C_8$-$C_{20}$ alkyl group, n is from about 1 to 20, and M is a salt-forming cation. In a specific embodiment, $R'$ is $C_{10}$-$C_{18}$ alkyl, n is from about 1 to 15, and M is sodium, potassium, ammonium, alkylammonium, or alkanolammonium. In more specific embodiments, $R'$ is a $C_{12}$-$C_{16}$, n is from about 1 to 6 and M is sodium. The alkyl ether sulfates will generally be used in the form of mixtures comprising varying $R'$ chain lengths and varying degrees of ethoxylation. Frequently such mixtures will inevitably also contain some non-ethoxylated alkyl sulfate materials, i.e., surfactants of the above ethoxylated alkyl sulfate formula wherein n=0.

Non-ethoxylated alkyl sulfates may also be added separately to the compositions of this invention and used as or in any anionic surfactant component which may be present. Specific examples of non-alkoyxylated, e.g., non-ethoxylated, alkyl ether sulfate surfactants are those produced by the sulfation of higher $C_8$-$C_{20}$ fatty alcohols. Conventional primary alkyl sulfate surfactants have the general formula: $R''OSO_3^-M^+$ wherein $R''$ is typically a $C_8$-$C_{20}$ alkyl group, which may be straight chain or branched chain, and M is a water-solubilizing cation. In specific embodiments, $R''$ is a $C_{10}$-$C_{15}$ alkyl group, and M is alkali metal, more specifically $R''$ is $C_{12}$-$C_{14}$ alkyl and M is sodium. Specific, non-limiting examples of anionic surfactants useful herein include: a) $C_{11}$-$C_{18}$ alkyl benzene sulfonates (LAS); b) $C_{10}$-$C_{20}$ primary, branched-chain and random alkyl sulfates (AS); c) $C_{10}$-$C_{18}$ secondary (2,3)-alkyl sulfates having following formulae:

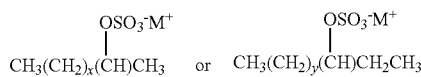

wherein M is hydrogen or a cation which provides charge neutrality, and all M units, whether associated with a surfactant or adjunct ingredient, can either be a hydrogen atom or a cation depending upon the form isolated by the artisan or the relative pH of the system wherein the compound is used, with non-limiting examples of preferred cations including sodium, potassium, ammonium, and mixtures thereof, and x is an integer of at least about 7, preferably at least about 9, and y is an integer of at least 8, preferably at least about 9; d) $C_{10}$-$C_{18}$ alkyl alkoxy sulfates ($AE_zS$) wherein preferably z is from 1-30; e) $C_{10}$-$C_{18}$ alkyl alkoxy carboxylates preferably comprising 1-5 ethoxy units; f) mid-chain branched alkyl sulfates as discussed in U.S. Pat. Nos. 6,020,303 and 6,060,443; g) mid-chain branched alkyl alkoxy sulfates as discussed in U.S. Pat. Nos. 6,008,181 and 6,020,303; h) modified alkylbenzene sulfonate (MLAS) as discussed in WO 99/05243, WO 99/05242, WO 99/05244, WO 99/05082, WO 99/05084, WO 99/05241, WO 99/07656, WO 00/23549, and WO 00/23548; i) methyl ester sulfonate (MES); j) alpha-olefin sulfonate (AOS), and k) high-solubility alkyl sulfate (HSAS).

Another exemplary type of anionic surfactant comprises neutralized fatty acids.

Various amounts of anionic surfactant are contemplated for use in the present surface treatment compositions. In one or more embodiments, the present fabric treatment compositions may comprise about 6% to about 40% of anionic surfactant, or about 8% to about 25% of anionic surfactant.

Cationic Polymer

Various cationic polymers are suitable for use in the present surface treatment composition, for example, all polymers typically used in liquid detergent products. In accordance with one or more embodiments, the cationic polymer comprises a molecular weight of up to about 10,000,000 daltons and charge density in the range of 0.05 to 25 meq/g when calculated at pH 7. Without being bound by theory, the molecular weight, charge density, and presence of hydrophobic areas within the polymer structure of the cationic polymer may affect the ability of the shielding salt to effectively prevent the polymer-surfactant complex from forming. In specific embodiments, the molecular weight of the cationic polymer is below 10,000,000, more preferably below 5,000,000, even more preferably below 1,000,000, and even more preferably below 600,000, and even more preferably about 500,000 daltons or below. Moreover, the charge density may be in the range of 0.05 to 25 meq/g when calculated at pH 7, or preferably below 7.0 meq/g, more preferably below 5.0 meq/g, and even more preferably below 3.0 meq/g when calculated at pH 7. As used herein, "charge density" refers to the charge density of the final polymer and may be different from the monomer feedstock. Charge density may be calculated by dividing the number of net charges per repeating unit by the molecular weight of the repeating unit and then multiplying by 1000. It should be noted that the positive charges may be located on the backbone of the cationic polymer and/or on the side chains of the cationic polymer. In the case of cationic polymers with amine monomers, the charge density depends on the pH of the carrier and thus the charge density for comparison with this disclosure should be measured at pH of 7.

Structurally, the cationic polymers may contain hydrophilic groups in addition to the cationic monomers. Without wishing to be bound by theory, it is believed the hydrophilic groups interrupt the hydrophobic areas of the cationic polymer, such as a hydrophobic hydrocarbon backbone, and thereby reduce hydrophobic interaction between the cationic polymer and the anionic surfactant. One non-limiting way to introduce hydrophilic groups as desired in preferred cationic polymers is to copolymerize a cationic monomer with a hydrophilic monomer. The hydrophilic monomer is preferably present at a minimum of 5 mole percent, more preferably at least 10 mole percent, and even more preferably at least 25 mole percent. Other methods of introducing hydrophilic groups known to those skilled in the art may also be utilized with non-limiting examples including using celluosic backbones, starches, or guars. Hydrophilic monomers are defined as having certain properties. A monomer is defined as being a hydrophilic monomer if it has one or more anionic charges at the pH of the product and/or is an uncharged monomer with a log P below 1 or for ionizable substances has a log D below 1. The log P and log D are more preferably below 0. The log P and log D are as calculated using Advanced Chemistry Development (ACD/Labs) Software V11.02 (1994-2011 ACD/Labs). As an example, vinylformamide co-monomer is calculated to have log D of 0.53 at pH 7 (less preferred), whereas acrylamide is calculated to have log D of −0.56 at pH 7 (more preferred) and acrylic acid is calculated at pH 7 to have log D of −2.56 (highly preferred).

For example, and not by way of limitation, the cationic polymer may comprise poly (diallyldimethylammonium chloride/co-acrylic acid), poly(acrylamide-methacrylamidopropyltrimethyl ammonium chloride), poly(acrylamide-methacrylamidopropyltrimethyl ammonium chloride/co-acrylic acid), poly(acrylamide-co-diallyldimethylammonium chloride/co-acrylic acid), poly (acrylamide-co-N,N,N-trimethyl aminoethyl acrylate), poly (diallyldimethylammonium chloride/co-vinyl alcohol), cationically modified hydroxyethylcellulose or any other polymer meeting the required characteristics. For poly(diallyldimethylammonium chloride/co-acrylic acid) the preferred ratio of diallyldimethylammonium chloride to acrylic acid is between approximately 90:10 and 50:50. The preferred cationic polymer is poly (diallyldimethylammonium chloride/co-acrylic acid) copolymer at a 65/35 mole ratio with a molecular weight of approximately 450,000. Poly (diallyldimethylammonium chloride/co-acrylic acid) copolymer may be further described by the nomenclature Polyquaternium-22 or PQ22 as named under the International Nomenclature for Cosmetic Ingredients.

Table 1 below includes cationic charge densities and monomer molecular weights for selected cationic polymers.

TABLE 1

| Polymer | Chemical description | Monomer molecular weight | Cationic charges per repeat unit | Charge density (meq/g) |
|---|---|---|---|---|
| Polyquaternium 22, neutralized | Poly (diallyldimethyl-ammonium chloride/co-acrylic acid) copolymer 65/35 mole ratio, neutralized with NaOH | 161.67 (DADMAC) 94.05 (acrylic acid, sodium neutralized) | 30 | 2.17 |
| Polyquaternium 22, un-neutralized | Poly (diallyldimethyl-ammonium chloride/co-acrylic acid) copolymer 65/35 mole ratio | 161.67 (DADMAC) 72.06 (acrylic acid) | 65 | 4.99 |

Various amounts of cationic polymer are contemplated for use in the present surface treatment compositions. In one or more embodiments, the present surface treatment compositions may comprise about 6% to about 40% of anionic surfactant, or about 6% to about 15% of cationic polymer. Moreover, as the present composition is directed to promoting the formation of coacervate in wash water upon dilution and preventing formation in the bottle, it is also beneficial to control the weight ratio of anionic surfactant to cationic polymer. The ratio of anionic surfactant to cationic polymer may be between about 0.5:1 and about 4:1, or between about 0.50:1 to about 3:1, or from about 0.75:1 to about 1.5:1.

Shielding Salt

As stated above, shielding salts are salts that sequester or maintain separation between anionic surfactants and cationic polymers inside the detergent container or bottle in order to reduce or eliminate coacervate formation inside the bottle. In accordance with the present invention, shielding salts are ionic species which form positively charged ions (cations) and negatively charged ions (anions) when dissolved in water. While various weights are contemplated as being within the scope of the present invention, the molecular weight of the shielding salt is between about 25 and about 500 daltons. Moreover, the shielding salt is not a strong base, which means the shielding salt is unable to deprotonate very weak acids in an acid/base reaction.

As further clarification, the shielding salt is not a surfactant, which, as defined herein, means the shielding salt is incapable of lowering the surface tension of water to below 50 mN/m when it is added to the water at concentrations up to 0.01M. As a reference point, water has a surface tension of 72 mN/m at room temperature.

In one or more embodiments, the shielding salt may comprise organic salts, inorganic salts, or combinations thereof. These inorganic mineral salts (herein also called simple salts) may comprise one or more halides of group IA and/or IIA metals, alkali and alkali earth metal salts, and mixtures thereof. For example and not by way of limitation, the simple salts may include NaCl, NaBr, NaI, NaNO3, and mixtures thereof. In one or more embodiments, the shielding salt may be an organic hydrotropic salt. While various organic hydrotropic salts are contemplated herein, the hydrotropic salts may include aromatic salts such as: ammonium-based, alkali and/or alkali earth salts of cumene sulfonate; ammonium-based, alkali and/or alkali earth salts of toluene sulfonate; ammonium-based, alkali and/or alkali earth salts of xylene sulfonate; ammonium-based, alkali and/or alkali earth salts of benzene sulfonate; other similar aromatic salts; and/or mixtures thereof. In exemplary embodiments, the shielding salt is sodium cumene sulfonate, sodium toluene sulfonate, sodium xylene sulfonate, sodium benzene sulfonate, and/or mixtures thereof. As would be familiar to the person of ordinary skill in the art, the shielding salt used in the composition may comprise a mixture of any of the salts listed in this paragraph and similar. While not excluded in all embodiments, the present shielding salts generally will not include boron.

The present surface treatment compositions may comprise about 4% to about 15%, or about 4 to about 10%, or about 6 to about 8% of shielding salt. Moreover, as the present composition is directed to promoting the formation of coacervate in wash water upon dilution and preventing formation in the bottle, it is also beneficial to control the weight ratio of anionic surfactant to cationic polymer. The weight ratio of shielding salt to cationic polymer is between about 0.3:1 and about 3:1, or about 0.6 to about 2:1.

Without wishing to be bound by theory, simple inorganic salts work mainly by screening electrostatic attraction which is enough to stabilize product which otherwise could form more hydrophilic surfactant polymer complexes as well as being generally effective in the case of weaker polymer-surfactant interactions. Hydrotropic salts, however, can both screen electrostatic attraction as well as disrupt the hydrophobic interaction. The hydrophobic interaction disruption is believed to be needed in the case of stronger surfactant/polymer interactions and/or more hydrophobic polymers. A portion or all the anions formed when the shielding salt is dissolved in water may have more than one negative charge. If more than one negative charge exists on at least a portion of the anions, it is preferable that no more than 50% of the negative charge of the portion of the anions having more than one negative charge is associated with carboxylate groups.

The shielding salt preferably will result in a percent transmittance (% T) of the composition of over 80%, or above 90% transmittance, or above about 90% transmittance at 580 nm. The measurement of the percent transmittance should be in the absence of any dyes, opacifying, or insoluble elements normally added to the composition. Opacifying or insoluble elements include elements such as structurants such as hydrogenated castor oil, silicones, aesthetic agents such as mica, and other elements which reduce percent transmittance.

Optional Additives

The surface treatment compositions of the invention may also contain additional adjunct cleaning additives. The precise nature of these additional components and levels of incorporation thereof will depend on the physical form of the composition, and the precise nature of the cleaning operation for which it is to be used.

The adjunct cleaning additives may be selected from the group consisting of nonionic surfactants, cationic surfactants, zwitterionic or amphoteric surfactants, builders, structurants or thickeners, clay soil removal/anti-redeposition agents, polymeric soil release agents, polymeric dispersing agents, polymeric grease cleaning agents, enzymes, enzyme stabilizing systems, bleaching compounds, bleaching agents, bleach activators, bleach catalysts, brighteners, dyes, mica, fabric hueing agents, dye transfer inhibiting agents, chelating agents, suds suppressors/anti-foams, fabric softeners, and perfumes, as well as such solvents, stabilizers, antimicrobial agents, and neutralizers required to formulate such product.

Compounds for reducing or suppressing the formation of suds can be incorporated into the compositions of the present invention. Suds suppression can be of particular importance in the so-called "high concentration cleaning process" as described in U.S. Pat. Nos. 4,489,455 and 4,489,574, and in front-loading-style washing machines.

To minimize or eliminate residue in the laundering equipment an anti-foam or anti-suds agent is beneficial. Anti-foam, anti-suds agent, and suds suppressor are interchangeable names for the same functional additive or additives. It is believed that suds and foaming during a wash cycle can result in residue of the surface treatment composition being deposited on the laundering equipment due to coacervate being entrapped in the suds. Residue is also believed to be minimized or eliminated by laundering small loads, using the delicate or equivalent cycle on the laundering equipment to minimize splashing, and/or using cold water in the laundering process.

A wide variety of materials may be used as suds suppressors, and suds suppressors are well known to those skilled in the art. See, for example, Kirk Othmer Encyclopedia of Chemical Technology, Third Edition, Volume 7, pages 430-447 (John Wiley & Sons, Inc., 1979). Examples of suds suppressors include monocarboxylic fatty acid and soluble salts therein, high molecular weight hydrocarbons such as paraffin, fatty acid esters (e.g., fatty acid triglycerides), fatty acid esters of monovalent alcohols, aliphatic $C_{18}$-$C_{40}$ ketones (e.g., stearone), N-alkylated amino triazines, waxy hydrocarbons preferably having a melting point below about 100° C., silicone suds suppressors, and secondary alcohols. Suds suppressors are described in U.S. Pat. Nos. 2,954,347; 4,265,779; 4,265,779; 3,455,839; 3,933,672; 4,652,392; 4,978,471; 4,983,316; 5,288,431; 4,639,489; 4,749,740; and 4,798,679; 4,075,118; European Patent Application No. 89307851.9; EP 150,872; and DOS 2,124,526.

The compositions herein will generally comprise from 0% to about 10% of suds suppressor. When utilized as suds suppressors, monocarboxylic fatty acids, and salts therein, will be present typically in amounts up to about 5%, by weight, of the surface treatment composition. Preferably, from about 0.5% to about 3% of fatty monocarboxylate suds suppressor is utilized. Silicone suds suppressors are typically utilized in amounts up to about 2.0%, by weight, of the detergent composition, although higher amounts may be used. Monostearyl phosphate suds suppressors are generally utilized in amounts ranging from about 0.1% to about 2%, by weight, of the composition. Hydrocarbon suds suppressors are typically utilized in amounts ranging from about 0.01% to about 5.0%, although higher levels can be used. The alcohol suds suppressors are typically used at 0.2%-3% by weight of the finished compositions.

Perfumes and perfumery ingredients useful in the present compositions and processes comprise a wide variety of natural and synthetic chemical ingredients, including, but not limited to, aldehydes, ketones, esters, and the like. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes typically comprise from about 0.01% to about 2%, by weight, of the surface treatment compositions herein, and individual lay softeners can be used in combination with amine and cationic softeners perfumery ingredients can comprise from about 0.0001% to about 90% of a finished perfume composition. In one aspect, the compositions disclosed herein may comprise a perfume delivery system. Suitable perfume delivery systems, methods of making certain perfume delivery systems and the uses of such perfume delivery systems are disclosed in USPA 2007/0275866 A1. In one aspect, such perfume delivery system may be a perfume microcapsule. In one aspect, said perfume microcapsule may comprise a core that comprises perfume and a shell, said shell encapsulating said core. In one aspect, said shell may comprise a material selected from the group consisting of aminoplast copolymer, esp. melamine-formaldehyde or urea-formaldehyde or cross-linked melamine formaldehyde, an acrylic, an acrylate and mixtures thereof. In one aspect, said perfume microcapsule's shell may be coated with one or more materials, such as a polymer, that aids in the deposition and/or retention of the perfume microcapsule on the site that is treated with the composition disclosed herein. In one aspect said polymer may be a cationic polymer selected from the group consisting of polysaccharides, cationically modified starch, cationically modified guar, polysiloxanes, poly diallyl dimethyl ammonium halides, copolymers of poly diallyl dimethyl ammonium chloride and vinyl pyrrolidone, acrylamides, imidazoles, imidazolinium halides, imidazolium halides, poly vinyl amine, copolymers of poly vinyl amine and N-vinyl formamide and mixtures thereof. In one aspect, said perfume microcapsule may be friable and/or have a mean particle size of from about 10 microns to about 500 microns or from about 20 microns to 200 microns. In one aspect, said composition may comprise, based on total composition weight, from about 0.01% to about 80%, from about 0.1% to about 50%, from about 1.0% to about 25% or from about 1.0% to about 10% of said perfume microcapsules. Suitable capsules may be obtained from Appleton Papers Inc., of Appleton, Wis. USA. Formaldehyde scavengers may also be used in or with such perfume microcapsules.

When combined with a detergent composition, the surface treatment compositions of the present invention may optionally comprise a builder. Built detergents typically comprise at least about 1 wt % builder, based on the total weight of the detergent. Liquid formulations typically comprise up to about 10 wt %, more typically up to 8 wt % of builder to the total weight of the detergent.

Detergent builders, when used, are typically silicates, to assist in controlling mineral, especially calcium and/or magnesium, hardness in wash water or to assist in the removal of particulate soils from surfaces. Suitable builders can be selected from the group consisting of phosphates and polyphosphates, especially the sodium salts; carbonates, bicarbonates, sesquicarbonates and carbonate minerals other than sodium carbonate or sesquicarbonate; organic mono-, di-, tri-, and tetracarboxylates especially water-soluble nonsurfactant carboxylates in acid, sodium, potassium or alkanolammonium salt form, as well as oligomeric or water-soluble low molecular weight polymer carboxylates including aliphatic and aromatic types; and phytic acid. These may be complemented by borates, e.g., for pH-buffering purposes, or by sulfates, especially sodium sulfate and any other fillers or carriers which may be important to the engineering of stable surfactant and/or builder-containing detergent compositions. Other detergent builders can be selected from the polycarboxylate builders, for example, copolymers of acrylic acid, copolymers of acrylic acid and maleic acid, and copolymers of acrylic acid and/or maleic acid and other suitable ethylenic monomers with various types of additional functionalities. Also suitable for use as builders herein are synthesized crystalline ion exchange materials or hydrates thereof having chain structure and a composition represented by the following general Formula I an anhydride form: $x(M_2O).ySiO_2.zM'O$ wherein M is Na and/or K, M' is Ca and/or Mg; y/x is 0.5 to 2.0 and z/x is 0.005 to 1.0 as taught in U.S. Pat. No. 5,427,711.

Structured liquids can either be internally structured, whereby the structure is formed by primary ingredients (e.g. surfactant material) and/or externally structured by providing a three dimensional matrix structure using secondary ingredients (e.g. polymers, clay and/or silicate material). The composition may comprise a structurant, preferably from 0.01 wt % to 5 wt %, from 0.1 wt % to 2.0 wt % structurant. The structurant is typically selected from the group consisting of diglycerides and triglycerides, ethylene glycol distearate, microcrystalline cellulose, cellulose-based materials, microfiber cellulose, biopolymers, xanthan gum, gellan gum, and mixtures thereof. A suitable structurant includes hydrogenated castor oil, and non-ethoxylated derivatives thereof. A suitable structurant is disclosed in U.S. Pat. No. 6,855,680. Such structurants have a thread-like structuring system having a range of aspect ratios. Other suitable structurants and the processes for making them are described in WO2010/034736.

The compositions of the present invention can also optionally contain water-soluble ethoxylated amines having clay soil removal and antiredeposition properties. Exemplary clay soil removal and antiredeposition agents are described in U.S. Pat. Nos. 4,597,898; 548,744; 4,891,160; European Patent Application Nos. 111,965; 111,984; 112,592; and WO 95/32272.

Known polymeric soil release agents, hereinafter "SRA" or "SRA's", can optionally be employed in the present surface treatment when combined with a detergent composition. If utilized, SRA's will generally comprise from 0.01% to 10.0%, typically from 0.1% to 5%, preferably from 0.2% to 3.0% by weight, of the composition.

Preferred SRA's typically have hydrophilic segments to hydrophilize the surface of hydrophobic fibers such as polyester and nylon, and hydrophobic segments to deposit upon hydrophobic fibers and remain adhered thereto through completion of washing and rinsing cycles thereby serving as an anchor for the hydrophilic segments. This can enable stains occurring subsequent to treatment with SRA to be more easily cleaned in later washing procedures.

SRA's can include, for example, a variety of charged, e.g., anionic or even cationic (see U.S. Pat. No. 4,956,447), as well as noncharged monomer units and structures may be linear, branched or even star-shaped. They may include capping moieties which are especially effective in controlling molecular weight or altering the physical or surface-active properties. Structures and charge distributions may be tailored for application to different fiber or textile types and for varied detergent or detergent additive products. Examples of SRAs are described in U.S. Pat. Nos. 4,968,451; 4,711,730; 4,721,580; 4,702,857; 4,877,896; 3,959,230; 3,893,929; 4,000,093; 5,415,807; 4,201,824; 4,240,918; 4,525,524; 4,201,824; 4,579,681; and 4,787,989; European Patent Application 0 219 048; 279,134 A; 457,205 A; and DE 2,335,044.

Polymeric dispersing agents can advantageously be utilized at levels from about 0.1% to about 7%, by weight, in the compositions herein, especially in the presence of zeolite and/or layered silicate builders. Suitable polymeric dispersing agents include polymeric polycarboxylates and polyethylene glycols, although others known in the art can also be used. For example, a wide variety of modified or unmodified polyacrylates, polyacrylate/maleates, or polyacrylate/methacrylates are highly useful. Examples of polymeric dispersing agents are found in U.S. Pat. No. 3,308,067, European Patent Application No. 66915, EP 193,360, and EP 193,360.

Soil suspension, grease cleaning, and particulate cleaning polymers may include the alkoxylated polyamines. Such materials include but are not limited to ethoxylated polyethyleneimine, ethoxylated hexamethylene diamine, and sulfated versions thereof. Polypropoxylated derivatives are also included. A wide variety of amines and polyalklyeneimines can be alkoxylated to various degrees, and optionally further modified to provide the abovementioned benefits. A useful example is 600 g/mol polyethyleneimine core ethoxylated to 20 EO groups per NH and is available from BASF.

Alkoxylated polycarboxylates such as those prepared from polyacrylates are useful herein to provide additional grease removal performance. Such materials are described in WO 91/08281 and PCT 90/01815. Chemically, these materials comprise polyacrylates having one ethoxy side-chain per every 7-8 acrylate units. The side-chains are of the formula —$(CH_2CH_2O)_m(CH_2)_nCH_3$ wherein m is 2-3 and n is 6-12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise from about 0.05% to about 10%, by weight, of the compositions herein.

Enzymes, including proteases, amylases, other carbohydrases, lipases, oxidases, and cellulases may be used as adjunct ingredients. Enzymes are included in the present cleaning compositions for a variety of purposes, including removal of protein-based, carbohydrate-based, or triglyceride-based stains from substrates, for the prevention of refugee dye transfer in fabric laundering, and for fabric restoration. Preferred selections are influenced by factors such as pH-activity and/or stability optima, thermostability, and stability to active detergents, builders and the like. In one or more embodiments, the compositions may comprise from 0% to 5%, or from about 0.01%-1% by weight of enzyme.

A range of enzyme materials and means for their incorporation into synthetic detergent compositions is also disclosed in WO 9307263 A; WO 9307260 A; WO 8908694 A; U.S. Pat. Nos. 3,553,139; 4,101,457; and U.S. Pat. No. 4,507,219. Enzyme materials useful for liquid detergent formulations, and their incorporation into such formulations, are disclosed in U.S. Pat. No. 4,261,868. Enzymes for use in detergents can be stabilized by various techniques. Enzyme stabilization techniques are disclosed and exemplified in U.S. Pat. Nos. 3,600,319 and 3,519,570; EP 199,405, EP 200,586; and WO 9401532 A.

The enzyme-containing compositions herein may optionally also comprise from about 0.001% to about 10%, preferably from about 0.005% to about 8%, most preferably from about 0.01% to about 6%, by weight of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the surface treatment composition.

When combined with a detergent composition, the surface treatment compositions herein may further contain bleaching agents or bleaching compositions containing a bleaching agent and one or more bleach activators. Bleaching agents will typically be at levels of from about 1 wt % to about 30 wt %, more typically from about 5 wt % to about 20 wt %, based on the total weight of the composition, especially for fabric laundering. If present, the amount of bleach activators will typically be from about 0.1 wt % to about 60 wt %, more typically from about 0.5 wt % to about 40 wt % of the bleaching composition comprising the bleaching agent-plus-bleach activator.

Examples of bleaching agents include oxygen bleach, perborate bleach, percarboxylic acid bleach and salts thereof, peroxygen bleach, persulfate bleach, percarbonate bleach, and mixtures thereof. Examples of bleaching agents are disclosed in U.S. Pat. No. 4,483,781, U.S. patent application Ser. No. 740,446, European Patent Application 0,133,354, U.S. Pat. No. 4,412,934, and U.S. Pat. No. 4,634,551.

Examples of bleach activators (e.g., acyl lactam activators) are disclosed in U.S. Pat. Nos. 4,915,854; 4,412,934; 4,634,551; 4,634,551; and 4,966,723.

Bleaching agents other than oxygen bleaching agents are also known in the art and can be utilized herein (e.g., photo-activated bleaching agents such as the sulfonated zinc and/or aluminum phthalocyanines (U.S. Pat. No. 4,033,718, incorporated herein by reference), or pre-formed organic peracids, such as peroxycarboxylic acid or salt thereof, or a peroxysulphonic acid or salt thereof. A suitable organic peracid is phthaloylimidoperoxycaproic acid. If used, household cleaning compositions will typically contain from about 0.025% to about 1.25%, by weight, of such bleaches, especially sulfonate zinc phthalocyanine.

Any optical brighteners or other brightening or whitening agents known in the art can be incorporated at levels typically from about 0.01% to about 1.2%, by weight, into the surface treatment compositions herein when combined with a cleaning composition. Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982). Specific nonlimiting examples of optical brighteners which are useful in the present compositions are those identified in U.S. Pat. No. 4,790,856 and U.S. Pat. No. 3,646,015.

The compositions of the present invention may include fabric hueing agents. Non-limiting examples include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof. In another aspect, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® (Milliken, Spartanburg, S.C., USA) Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colorants, alkoxylated thiophene polymeric colourants, and mixtures thereof. Non-limiting examples of useful hueing dyes include those found in U.S. Pat. No. 7,205,269; U.S. Pat. No. 7,208,459; and U.S. Pat. No. 7,674,757 B2. For example, hueing dye may be selected from the group of: triarylmethane blue and violet basic dyes, methine blue and violet basic dyes, anthraquinone blue and violet basic dyes, azo dyes basic blue 16, basic blue 65, basic blue 66 basic blue 67, basic blue 71, basic blue 159, basic violet 19, basic violet 35, basic violet 38, basic violet 48, oxazine dyes, basic blue 3, basic blue 75, basic blue 95, basic blue 122, basic blue 124, basic blue 141, Nile blue A and xanthene dye basic violet 10, an alkoxylated triphenylmethane polymeric colorant; an alkoxylated thiopene polymeric colorant; thiazolium dye; and mixtures thereof. Preferred hueing dyes include the whitening agents found in WO 08/87497 A1 and those described in US 2008 34511 A1 (Unilever). A preferred agent is "Violet 13".

The compositions of the present invention when combined with a cleaning composition may also include one or more materials effective for inhibiting the transfer of dyes from one fabric to another during the cleaning process. Generally, such dye transfer inhibiting agents include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents typically comprise from about 0.01% to about 10% by weight of the composition, preferably from about 0.01% to about 5%, and more preferably from about 0.05% to about 2%. When combined with a detergent composition, the surface treatment compositions herein may also optionally contain one or more iron and/or manganese and/or other metal ion chelating agents. Such chelating agents can be selected from the group consisting of amino carboxylates, amino phosphonates, polyfunctionally-substituted aromatic chelating agents and mixtures therein. If utilized, these chelating agents will generally comprise from about 0.1% to about 15% by weight of the detergent compositions herein. More preferably, if utilized, the chelating agents will comprise from about 0.1% to about 3.0% by weight of such compositions.

The chelant or combination of chelants may be chosen by one skilled in the art to provide for heavy metal (e.g. Fe) sequestration without negatively impacting enzyme stability through the excessive binding of calcium ions. Non-limiting examples of chelants of use in the present invention are found in U.S. Pat. Nos. 7,445,644, 7,585,376 and 2009/0176684 A1.

Useful chelants include heavy metal chelating agents, such as diethylenetriaminepentaacetic acid (DTPA) and/or a catechol including, but not limited to, tiron. In embodiments in which a dual chelant system is used, the chelants may be DTPA and tiron. Other chelating agents suitable for use herein can be selected from the group consisting of aminocarboxylates, aminophosphonates, polyfunctionally-substituted aromatic chelating agents and mixtures thereof. Chelants particularly of use include, but are not limited to: HEDP (hydroxyethanedimethylenephosphonic acid); MGDA (methylglycinediacetic acid); and mixtures thereof.

Aminocarboxylates useful as chelating agents include, but are not limited to, ethylenediaminetetracetates, N-(hydroxyethyl)ethylenediaminetriacetates, nitrilotriacetates, ethylenediamine tetraproprionates, triethylenetetraaminehexacetates, diethylenetriamine-pentaacetates, and ethanoldiglycines, alkali metal, ammonium, and substituted ammonium salts thereof and mixtures thereof. Aminophosphonates are also suitable for use as chelating agents in the compositions of the invention when at least low levels of total phosphorus are permitted in detergent compositions, and include ethylenediaminetetrakis (methylenephosphonates). Preferably, these aminophosphonates do not contain alkyl or alkenyl groups with more than about 6 carbon atoms. Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A biodegradable chelator for use herein is ethylenediamine disuccinate ("EDDS"), especially (but not limited to) the [S,S] isomer as described in U.S. Pat. No. 4,704,233. The trisodium salt is preferred though other forms, such as magnesium salts, may also be useful. The chelant system may be present in the surface treatment compositions of the present invention at from about 0.2% to about 0.7% or from about 0.3% to about 0.6% by weight of the surface treatment compositions disclosed herein.

Various through-the-wash fabric softeners, especially the impalpable smectite clays of U.S. Pat. No. 4,062,647, as well as other softener clays known in the art, can optionally be used typically at levels of from about 0.5% to about 10% by weight in the present compositions to provide fabric softener benefits concurrently with fabric cleaning. Clay softeners can be used in combination with amine and cationic softeners as disclosed, for example, in U.S. Pat. No. 4,375,416, and U.S. Pat. No. 4,291,071. Cationic softeners can also be used without clay softeners.

Additionally, the surface treatment compositions may optionally include nonionic surfactant in addition to anionic surfactant. For the purposes of this invention nonionic surfactants may be defined as substances with molecular structures consisting of a hydrophilic and hydrophobic part. The hydrophobic part consists of a hydrocarbon and the hydrophilic part of a strongly polar group. The nonionic surfactants of this invention are soluble in water. The most preferred nonionic surfactants are alkoxylated, preferably ethoxylated, compounds and carbohydrate compounds. Examples of suitable ethoxylated surfactants include ethoxylated alcohols, ethoxylated alkyl phenols, ethoxylated fatty amides, and ethoxylated fatty esters. Preferred nonionic ethoxylated surfactants have an HLB of from about 10 to about 20. It is advantageous if the surfactant alkyl group contains at least 12 carbon atoms.

Examples of suitable carbohydrate surfactants or other polyhydroxy surfactants include alkyl polyglycosides as disclosed in EP 199 765A and EP 238 638A, polyhydroxy amides as disclosed in WO 93/18125A and WO 92/06161A, fatty acid sugar esters (sucrose esters), sorbitan ester ethoxylates, and poly glycerol esters and alkyl lactobionamides. Preferred nonionic surfactants are these having a long alkyl chain (C12-C22) and ethoxylated with 10 to 25 moles of ethylene oxide. Especially preferred nonionic surfactants include tallow alcohol ethoxylated with 15 or 20 moles of ethylene oxide and coco alcohol ethoxylated with 15 or 20 moles of ethylene oxide. Preferred viscosities are achieved when the ratio of polymeric nonionic surfactant to long chain nonionic surfactant is from 10:1 to 1:50, more preferably 5:1 to 1:30, most preferably 3:1 to 1:3.

Additionally, the surface treatment compositions may optionally include cationic surfactant in addition to anionic surfactant. Non-limiting examples of cationic surfactants include: the quaternary ammonium surfactants, which can have up to 26 carbon atoms include: alkoxylate quaternary ammonium (AQA) surfactants as discussed in U.S. Pat. No. 6,136,769; dimethyl hydroxyethyl quaternary ammonium as discussed in U.S. Pat. No. 6,004,922; dimethyl hydroxyethyl lauryl ammonium chloride; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239,660 4,260, 529 and U.S. Pat. No. 6,022,844; and amino surfactants as discussed in U.S. Pat. No. 6,221,825 and WO 00/47708, specifically amido propyldimethyl amine (APA).

Additionally, the surface treatment compositions may optionally include amphoteric or zwitterionic surfactant in addition to anionic surfactant. Non-limiting examples of zwitterionic or ampholytic surfactants include: derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 at column 19, line 38 through column 22, line 48, for examples of zwitterionic surfactants; betaines, including alkyl dimethyl betaine and cocodimethyl amidopropyl betaine, $C_8$ to $C_{18}$ (for example from $C_{12}$ to $C_{18}$) amine oxides and sulfo and hydroxy betaines, such as N-alkyl-N,N-dimethylammino-1-propane sulfonate where the alkyl group can be $C_8$ to $C_{18}$ and in certain embodiments from $C_{10}$ to $C_{14}$. Non-limiting examples of ampholytic surfactants include: aliphatic derivatives of secondary or tertiary amines, or aliphatic derivatives of heterocyclic secondary and tertiary amines in which the aliphatic radical can be straight- or branched-chain. One of the aliphatic substituents may contain at least about 8 carbon atoms, for example from about 8 to about 18 carbon atoms, and at least one contains an anionic water-solubilizing group, e.g. carboxy, sulfonate, sulfate. See U.S. Pat. No. 3,929,678 at column 19, lines 18-35, for suitable examples of ampholytic surfactants.

EXAMPLES

Testing of the various shielding salts were conducted using formulations listed in Table 2 below without any opacifying or insoluble ingredients normally added.

TABLE 2

|  | Formula A, wt % | Formula B, wt % |
|---|---|---|
| AES (C12-15 chain, 1.8 EO) | 11.2 | 11.2 |
| Nonionic surfactant (12-14 chain, 9EO) | 3.5 | 0.0 |
| Propane-diol | 4.4 | 3.1 |
| DTPA, sodium neutralized | 0.3 | 0.3 |
| monoethanolamine (MEA) | 1.1 | 1.2 |
| diethyleneglycol (DEG) | 0.8 | 0.8 |
| NaOH | 1.5 | 0.3 |
| Borax | 0.4 | 0.4 |
| LAS (11.8 chainlength) | 0 | 0 |
| Citric acid | 1.8 | 1.8 |
| Fatty acid | 1.1 | 1.1 |
| Shielding salt | variable | variable |
| Ethanol | 4.5 | 3.5 |
| Water | balance | balance |
| PQ22 (poly(diallyldimethylammonium-chloride/co-acrylic acid) copolymer 65/35 mole ratio, 450,000 MW) | 11.8 | 11.8 |
| Perfume | 0.7 | 0.7 |
| PP5495 (silicone softening agent) | 2.0 | 2.0 |
| Colorant, mica, hydrogenated castor oil, silicone suds suppressor, and associated solvents | 7.7% (not added to formula when measuring % T) | 7.7% (not added to formula when measuring % T) |

Sodium cumene sulfonate demonstrates high percent transmittance when tested according to formula A listed above.

TABLE 3

| Weight Percent % sodium cumene sulfonate | | | | | | | | | |
|---|---|---|---|---|---|---|---|---|---|
| 0.0 | 1.3 | 2.6 | 3.9 | 4.7 | 5.2 | 5.7 | 6.3 | 7.8 | 9.5 |
| Percent Transmittance | | | | | | | | | |
| % T @ 580 nm | | | | | | | | | |
| 17.6 | 44.3 | 80.0 | 86.9 | 91.8 | 96.5 | 98.2 | 98.1 | 99.3 | 93.7 |

Sodium toluene sulfonate and sodium xylene sulfonate demonstrate high percent transmittance when tested according to formula B listed above.

TABLE 4

| Weight Percent % sodium toluene sulfonate | | | | | |
|---|---|---|---|---|---|
| 0 | 1 | 3 | 5 | 7 | 9 |
| Percent Transmittance | | | | | |
| % T @ 580 nm | | | | | |
| 8.0 | 8.6 | 7.8 | 8.9 | 83.5 | 94.3 |

| Weight Percent % sodium xylene sulfonate | | | | | |
|---|---|---|---|---|---|
| 0 | 1 | 3 | 5 | 7 | 9 |
| Percent Transmittance | | | | | |
| % T @ 580 nm | | | | | |
| 8.0 | 5.9 | 8.4 | 6.4 | 98.8 | 90.2 |

At low levels of sodium cumene sulfonate, such as 2 wt %, high levels of PQ22 polymer are unstable and result in low percent transmittance. High levels of PQ22 polymer can be successfully formulated when a sufficient level of shielding salt is formulated. A sufficient level of shielding salt includes 8% by weight of the composition. Testing samples were prepared according to formula B listed above with additional water making up the difference between 8 and 11.8% examples.

TABLE 5

| | Weight Percent | | | |
|---|---|---|---|---|
| % PQ22 | 8.0 | 11.8 | 8.0 | 11.8 |
| % sodium cumene sulfonate | 2.000 | 2.000 | 8.000 | 8.000 |
| | Percent Transmittance | | | |
| % T @ 580 nm | 52.8 | 58.6 | >99 | >99 |

As used herein, the term "comprising" means various components conjointly employed in the preparation of the composition or methods of the present disclosure. Accordingly, the terms "consisting essentially of" and "consisting of" are embodied in the term "comprising". As used herein, the articles including "the", "a" and "an" when used in a claim or in the specification, are understood to mean one or more of what is claimed or described. As used herein, the terms "include", "includes" and "including" are meant to be non-limiting.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A surface treatment composition comprising:
   a) from about 6% to about 20%, by weight of the composition, of cationic polymer wherein the cationic polymer is poly(diallyldimethylammonium chloride/co-acrylic acid) copolymer (polyquaternium-22);

b) from about 6% to about 40%, by weight of the composition, of anionic surfactant; and c) from about 4% to about 15%, by weight of the composition, of a shielding salt, wherein the shielding salt:
has a molecular weight of from about 25 to about 500 and is incapable of lowering the surface tension of water below 50 mN/m when added to water at concentrations of up to 0.01M;

wherein the weight ratio of anionic surfactant to cationic polymer is between about 0.5:1 and about 4:1, and wherein the weight ratio of shielding salt to cationic polymer is between about 0.3:1 and about 3:1.

2. The composition according to claim 1, wherein the shielding salt is characterized in that it forms anions when dissolved in water, wherein at least a portion of the anions have more than one negative charge, and wherein no more than 50% of the negative charge of the portion of the anions having more than one negative charge is associated with carboxylate groups.

3. The composition according to claim 1, wherein the shielding salt is selected from the group consisting of: ammonium-based, alkali or alkali earth salts of cumene sulfonate; ammonium-based, alkali or alkali earth salts of toluene sulfonate; ammonium-based, alkali or alkali earth salts of xylene sulfonate; ammonium-based, alkali or alkali earth salts of benzene sulfonate; and mixtures thereof.

4. The composition according to claim 1, wherein the shielding salt is selected from the group consisting of sodium cumene sulfonate, sodium toluene sulfonate, sodium xylene sulfonate, sodium benzene sulfonate, and mixtures thereof.

5. A composition according to claim 1, wherein the shielding salt comprises sodium cumene sulfonate.

6. A composition according to claim 1, wherein the shielding salt does not comprise boron.

7. A composition according to claim 1, further comprising an anti-foam agent.

8. The composition according to claim 1, wherein the charge density of the cationic polymer is between 0.05 meq/g and 25 meq/g.

9. The composition according to claim 1, wherein the molecular weight of the cationic polymer is below 10,000,000.

10. The composition according to claim 9, wherein the molecular weight of the cationic polymer is about 500,000 or below.

11. The composition according to claim 1, wherein the composition has a percent transmittance (% T) of over 80% in the absence of any dyes, opacifying elements, or insoluble elements.

* * * * *